(12) United States Patent
Eom et al.

(10) Patent No.: US 10,321,874 B2
(45) Date of Patent: Jun. 18, 2019

(54) MOBILE HEALTHCARE DEVICE AND METHOD OF OPERATING THE SAME

(71) Applicant: SAMSUNG ELECTRONICS CO., LTD., Suwon-si (KR)

(72) Inventors: Kunsun Eom, Seoul (KR); Kak Namkoong, Seoul (KR); Yeolho Lee, Anyang-si (KR); Myounghoon Jung, Bucheon-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 94 days.

(21) Appl. No.: 14/698,976

(22) Filed: Apr. 29, 2015

(65) Prior Publication Data
US 2016/0113578 A1  Apr. 28, 2016

(30) Foreign Application Priority Data
Oct. 23, 2014 (KR) .......... 10-2014-0144288

(51) Int. Cl.
*A61B 5/00* (2006.01)
*A61B 5/053* (2006.01)
*A61B 5/05* (2006.01)
(Continued)

(52) U.S. Cl.
CPC .......... *A61B 5/681* (2013.01); *A61B 5/0537* (2013.01); *A61B 5/742* (2013.01); *G06F 19/3418* (2013.01); *G16H 40/63* (2018.01); *A61B 5/0402* (2013.01); *A61B 5/053* (2013.01); *A61B 5/4869* (2013.01); *A61B 5/4872* (2013.01);
(Continued)

(58) Field of Classification Search
CPC ....... A61B 5/681; A61B 5/053; A61B 5/0537; A61B 5/742; A61B 5/4869; A61B 5/4872; A61B 5/6898; A61B 5/7425; A61B 5/743; A61B 5/7435; A61B 5/744; A61B 5/6831;
(Continued)

(56) References Cited

U.S. PATENT DOCUMENTS

| 2011/0237963 A1* | 9/2011 | Nishioka ............... A61B 5/022 600/493 |
| 2013/0215042 A1* | 8/2013 | Messerschmidt ....... G06F 3/041 345/173 |
| 2013/0218582 A1* | 8/2013 | LaLonde ............... A61B 5/686 705/2 |
| 2014/0073983 A1* | 3/2014 | Vogel .................. A61B 5/0537 600/547 |

(Continued)

FOREIGN PATENT DOCUMENTS

| JP | 2007-117270 A | 5/2007 |
| JP | 4600170 B2 | 12/2010 |

(Continued)

OTHER PUBLICATIONS

English translation of WO 2013/179848 A1.*

*Primary Examiner* — Devin B Henson
(74) *Attorney, Agent, or Firm* — Sughrue Mion, PLLC

(57) ABSTRACT

A mobile healthcare device and method of operating the same are provided. The method includes setting a mode of the mobile healthcare device to a measurement mode, displaying a screen for guiding a user to maintain a predetermined position during the measurement mode, and, in response to a predetermined amount of time passing from a time at which the screen begins to be displayed, obtaining state information of the user based on bio information of the user, the bio information being received from a sensor.

16 Claims, 11 Drawing Sheets

(51) Int. Cl.
  *G06F 19/00* (2018.01)
  *G16H 40/63* (2018.01)
  *A61B 5/0402* (2006.01)

(52) U.S. Cl.
  CPC .............. *A61B 5/683* (2013.01); *A61B 5/684* (2013.01); *A61B 5/6831* (2013.01); *A61B 5/6843* (2013.01); *A61B 5/6898* (2013.01); *A61B 5/743* (2013.01); *A61B 5/744* (2013.01); *A61B 5/7425* (2013.01); *A61B 5/7435* (2013.01)

(58) Field of Classification Search
  CPC ....... A61B 5/6843; A61B 5/684; A61B 5/683; G06F 19/3406; G06F 19/3418
  See application file for complete search history.

(56) References Cited

U.S. PATENT DOCUMENTS

| | | | |
|---|---|---|---|
| 2015/0031964 A1* | 1/2015 | Bly | A61B 5/165 |
| | | | 600/301 |
| 2015/0109105 A1* | 4/2015 | Shimizu | A61B 5/117 |
| | | | 340/5.82 |

FOREIGN PATENT DOCUMENTS

| | | | |
|---|---|---|---|
| KR | 10-0330746 B1 | 4/2002 | |
| KR | 10-1000467 B1 | 12/2010 | |
| KR | 10-2013-0111713 A | 10/2013 | |
| WO | WO 2013179848 A1 * | 12/2013 | A61B 5/117 |

* cited by examiner

MOBILE HEALTHCARE DEVICE AND METHOD OF OPERATING THE SAME

CROSS REFERENCE TO RELATED APPLICATION

This application claims priority from Korean Patent Application No. 10-2014-0144288, filed on Oct. 23, 2014 in the Korean Intellectual Property Office, the disclosure of which is incorporated herein in its entirety by reference.

BACKGROUND

1. Field

Apparatuses and methods consistent with exemplary embodiments relate to a healthcare device configured to measure bio information and a method of operating the same.

2. Description of the Related Art

With the developments in medical science and the increase in life expectancy of people, interest in health care and medical devices has rapidly increased. Accordingly, an amount of various medical devices for use in hospitals, inspection agencies, medical offices, and the like, has grown. For example, medium-sized medical devices such as those installed in government agencies, small-sized medical devices, personal mobile healthcare devices, and the like, have been proposed.

Because the size of the healthcare devices has been reduced, it is easier for a user to carry or wear them. However, user's bio information can typically only be properly acquired using such devices when the user maintains a certain position according to types of bio information to be acquired.

SUMMARY

One or more exemplary embodiments provide a mobile healthcare device configured to display a dynamic screen to inform a user to maintain a certain posture when bio information is acquired, and a method of operating the mobile healthcare device.

According to an aspect of an exemplary embodiment, there is provided a method of operating a mobile healthcare device, the method including setting a mode of the mobile healthcare device to a measurement mode; displaying a screen for guiding a user to maintain a predetermined position during the measurement mode, and, in response to a predetermined amount of time passing from a time at which the screen begins to be displayed, obtaining state information of the user based on bio information of the user, the bio information being received from a sensor.

The predetermined position of the user may indicate a contact state of the sensor at a predetermined area of the user.

The screen may be displayed in response to a position of the user being the predetermined position.

The position of the user may be determined using an impedance output from the sensor.

The predetermined amount of time may range from about two seconds to about ten seconds.

The obtaining may be performed after the displaying is terminated.

The obtaining may be performed during the displaying.

The screen may display numbers that change according to time.

The numbers may sequentially and continuously change in an ascending order or descending order.

The method may further include storing user information including at least one of a height, a gender, and a weight of the user.

The method may further include matching the state information with the user information and storing the state information and the user information, in response to the measurement mode being a user mode.

The method may further include discarding the state information and the user information in response to the measurement mode being a guest mode.

The state information and the user information may be discarded in response to the measurement mode being terminated.

The bio information may include a body impedance, and the state information may include a bio composition of the user.

The body composition may include at least one of body fat, a skeletal muscle mass, a muscle mass, a degree of obesity, a muscle strength, an edema value, a body composition ratio, and an amount of intra-abdominal fat.

According to an aspect of another exemplary embodiment, there is provided a mobile healthcare device including a sensor configured to detect bio information of a user; a display configured to display a screen for guiding the user to maintain a predetermined position, and a processor configured to obtain state information of the user based on the bio information received from the sensor in response to a predetermined amount of time passing from a time at which the screen begins to be displayed.

The predetermined position of the user may indicate a contact state of the sensor at a predetermined area of the user.

The screen may be displayed in response to a position of the user being the predetermined position.

The screen may display numbers that change according to time.

The bio information may include a body impedance of the user, and the state information may include a body composition of the user.

BRIEF DESCRIPTION OF THE DRAWINGS

The above and/or other aspects will become apparent and more readily appreciated from the following description of exemplary embodiments, taken in conjunction with the accompanying drawings, in which.

DETAILED DESCRIPTION

Figure 1:
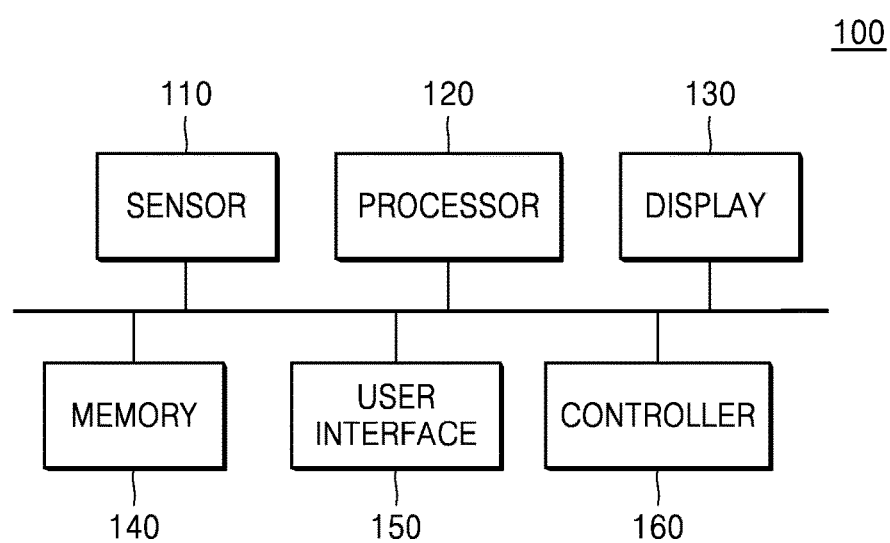
FIG. 1 is a block diagram of a mobile healthcare device according to an exemplary embodiment.

The terms used in this specification may be general terms that are widely used in the art in consideration of the functions regarding the inventive concept, but the terms may vary according to the intention of those of ordinary skill in the art, precedents, new technology in the art, and the like. Also, specified terms may be selected by the applicant, and the detailed meaning thereof will be described in the detailed description of the inventive concept. Thus, the terms used in the specification may be understood not as simple names but based on the meaning of the terms and the overall description of the invention.

Throughout the specification, when a region is referred to as being connected to another region, the region may be directly connected to the other region or one or more intervening layers may exist therebetween. Also, when a portion includes an element, another element may be further included, rather than excluding the existence of the other element, unless otherwise described. Also, terms such as ". . . unit", ". . . module", and the like, may be units for processing at least one function or operation and may be implemented as hardware, software, or a combination of hardware and software.

In the present specification, it is understood that terms such as "including", "having", and "comprising" are intended to indicate the existence of the features, numbers, steps, actions, components, parts, or combinations thereof disclosed in the specification, and they are not intended to preclude the possibility that one or more other features, numbers, steps, actions, components, parts, or combinations thereof may exist or may be added.

The inventive concept is more fully described herein with reference to the accompanying drawings, in which exemplary embodiments of the invention are shown. The invention may, however, be embodied in many different forms and should not be construed as being limited to the embodiments set forth herein. Rather, these exemplary embodiments are provided so that this disclosure will be thorough and complete, and will fully convey the concept of the invention to those skilled in the art.

According to various embodiments, a mobile healthcare device or apparatus may refer to a portable type or a wearable type. For example, the mobile healthcare device may be of a watch type, a bracelet type, a ring type, a hair band type, and the like, and may have communication and data processing functions. In one or more exemplary embodiments of the inventive concept, the mobile healthcare device is a watch-type device or a wristband-type device, but is not limited thereto.

Also, the mobile healthcare device may have a housing or a plurality of housings. For example, in the case of the mobile healthcare device having a plurality of housings, a plurality of components may be respectively connected to the plurality of housings in a wired or wireless manner. For example, the components may be arranged into a first device which includes a sensor disposed on a wrist, etc. of the user and which detects bio information, and a second device which processes the detected bio information. The mobile healthcare device may be included in another device, for example, a mobile terminal, which performs other functions. The mobile terminal may include a mobile phone, a tablet, a computer, an appliance, a game console, and the like.

FIG. 1 is a block diagram of a mobile healthcare device 100, according to an embodiment. As shown in FIG. 1, the mobile health-care device 100 includes a sensor 110 which detects bio information of a user, a processor 120 which obtains state information based on the bio information received from the sensor 110, a display 130 which displays the obtained state information, a memory 140 which stores a program, and the like, which may be used by the mobile healthcare device 100, a user interface 150 which receives a user command, and the like, and a controller 160 which controls components in the mobile health care device 100.

The user is a target from whose bio information is to be detected. The user may be a person or an animal or some portions of a person or an animal. The bio information represents distinctive signals generated by the user, for example, signals obtained from an electrocardiogram (ECG), a ballistocardiogram (BCG), a photoplethysmograph (PPG), an electromyogram, or movements of a certain part (for example, the heart, muscle, etc.) of the user, or may be information representing the blood sugar level, cholesterol, body impedance, and the like. The state information may indicate a health state of the user and is obtained using the bio information. For example, the state information may be the maximum blood pressure, minimum blood pressure, and the like, and may be obtained using the bio information such as the ECG, PPG, and the like. In addition, the state information indicating body composition may be obtained using bio information indicating the body impedance.

The sensor 110 may detect the bio information of the user. The sensor 110 may be disposed on, for example, on the wrist, chest, and/or ankle of the user. The sensor 110 may detect the bio information through a non-invasive method. For example, the sensor 110 may include a plurality of electrodes in which at least some of the electrodes may contact the user while the user wears the mobile healthcare device 100. Thus, the sensor 110 may detect the bio information by detecting electrical signals that vary with a change of the bio information, for example, a change of the body impedance. As another example, the sensor 110 may detect the bio information using reflected signals by irradiating light on the user or by using magnetic signals, pressure, or the like.

The processor 120 may obtain state information using the bio information. The processor 120 may convert the state information into images, texts, audio, and the like. The processor 120 may be a single micro processor module or a combination of two or more micro processor modules, however, the processor 120 is not limited thereto. Hereinafter, measuring the bio information may refer to the sensor 110 that detects the bio information, and the processor 120 that uses the detected bio information in order to obtain the state information.

The processor 120 may use various methods for obtaining the state information according to the types of the bio information. For example, when the bio information is the body impedance, the processor 120 may use the bio impedance and obtain the body composition of the user. The body composition may include body fat, characteristics of skin (for example, moisture of the body), muscle strength, an edema value, skeletal muscle mass, muscle mass, a degree of obesity, a body composition ratio, an amount of intra-abdominal fat, and the like, of the user. As another example, the processor 120 may obtain the body composition using the body impedance as well as user information. The user information may refer to an age, weight, height, gender, etc. of the user.

As another example, when the bio information is ECG signals according to a heart's activity, the processor 120 may obtain the state information from the bio information, which is in a wave form, and blood pressure of the user may be analyzed using the wave form of the bio information. The wave form of the bio information may be a function according to time. When the wave form of the bio information is obtained, the processor 120 may amplify the ECG signals and may filter the amplified ECG signals using a FirBand-pass filter. Here, peaks may be detected from the filtered ECG signals, and the wave form of the bio information may be obtained by adaptively filtering the detected peaks.

The display 130 may output the bio information after the ECG signals or other user information has been processed. The display 130 may display a user interface (UI), a graphic UI (GUI), and the like, for displaying the state information, a use protocol of the mobile healthcare device 100, and the like. The display 130 may include at least one of a liquid crystal display (LCD), a thin film transistor-liquid crystal display, an organic light-emitting diode (OLED), a flexible display, and a three-dimensional (3D) display. In some examples there may be two or more displays 130 according to the type of the mobile health care device 100.

The display 130 and a touch pad for receiving a user input may have an interlayer structure and may form a touch screen. In this example, the display 130 may be used as an input device and an output device.

The memory 140 may store data generated while the mobile healthcare device 100 operates. For example, the memory 140 may be a storage medium such as a hard disk drive (HDD), read only memory (ROM), random access memory (RAM), flash memory, a memory card, and the like.

The user interface 150 may receive an input for manipulating the mobile health-care device 100 from the user and may output bio information processed by the user interface 150. For example, the user interface 150 may include a button, a key pad, a switch, a dial, a touch interface, a camera, for manipulating the mobile healthcare device 100. The user interface 150 may include the display 130 for displaying an image and may be implemented as a touch screen.

The controller 160 may control overall operations of the mobile healthcare device 100. For example, the controller 160 may control the sensor 110 to detect the bio information. Also, the controller 160 may determine whether the detected bio information is normal or abnormal and may provide the user with a determination result through the display 130.

In an example in which the controller 160 requires the user or the user otherwise attempts to maintain a certain position in order to measure the bio information, the controller 160 may control the display 130 to display a guidance screen or dynamic screen to assist the user in maintaining the certain or predetermined position.

For example, when the mobile healthcare device 100 is a device for measuring the body impedance, the sensor 110 may include one or more electrodes to provide electrical signals to the user and receive the electrical signals from the user. When the body impedance is measured, the one or more electrodes may contact the user.

Figure 2A:
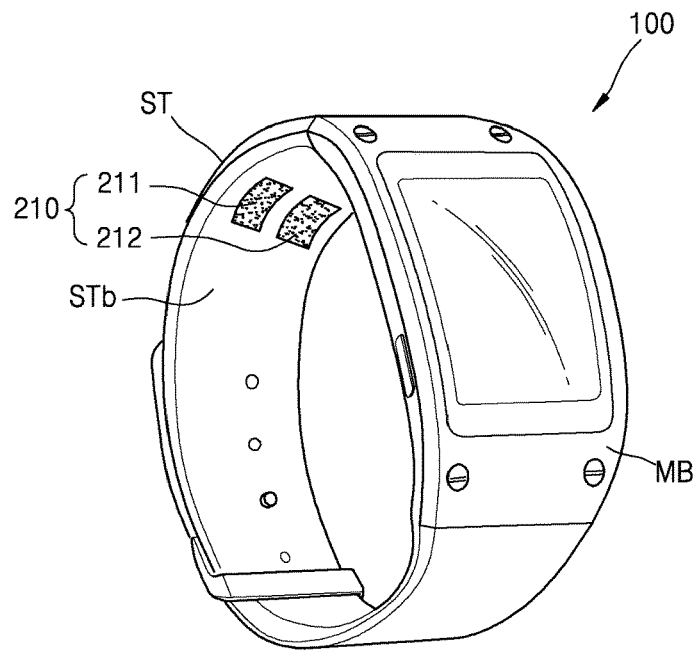
FIGS. 2A and 2B are perspective views of a mobile healthcare device for measuring body impedance, according to exemplary embodiments.
Figure 2B:
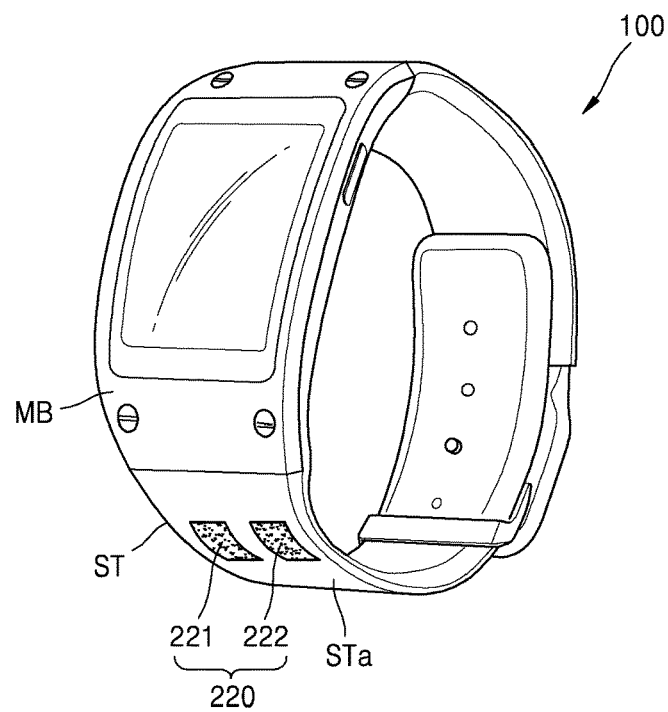
Figure 3:
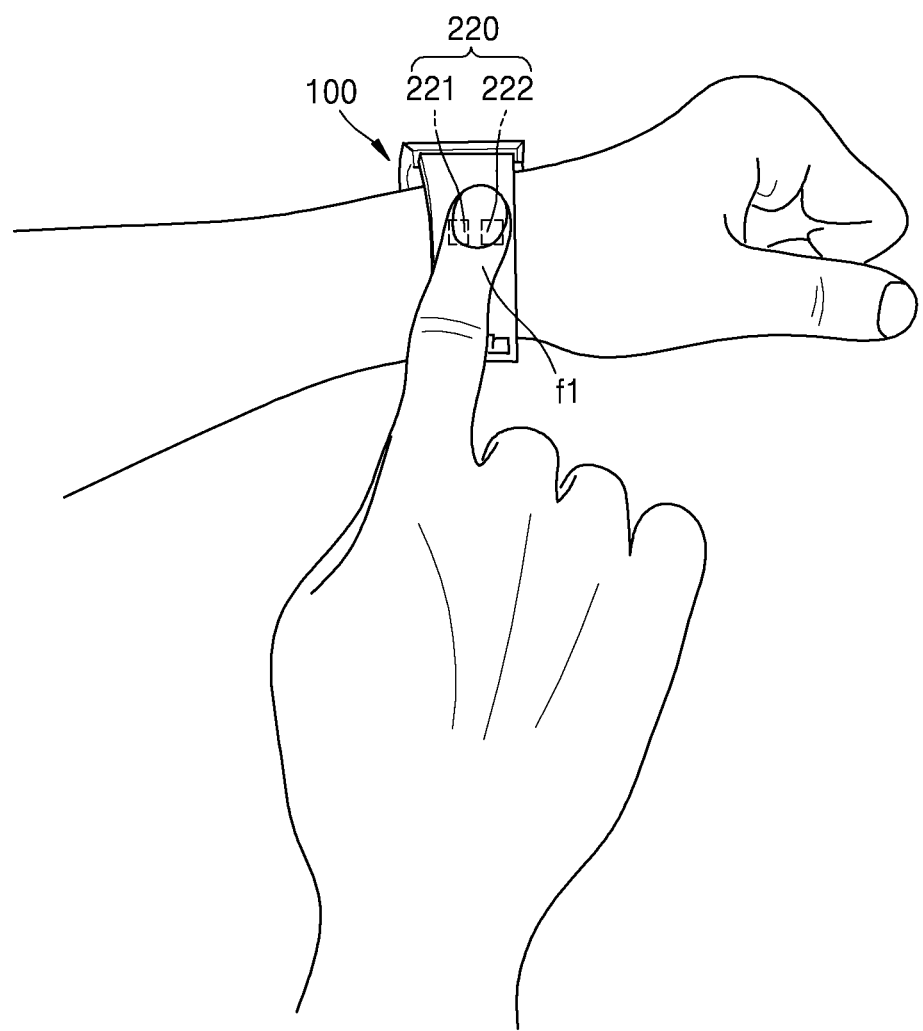
FIG. 3 shows an example of a position for measuring body impedance using the mobile healthcare device, according to an exemplary embodiment.

FIGS. 2A and 2B show perspective views of the mobile health-care device 100 when the body impedance is measured according to exemplary embodiments, and FIG. 3 shows an example of a position for measuring the body impedance using the mobile healthcare device 100, according to an exemplary embodiment. Referring to FIGS. 2A and 2B, the mobile healthcare device 100 includes a main body (MB) and straps ST that form a watch or other wearable device. There are two straps ST at both sides of the main body MB, and the user may wear the mobile health care device 100 after the straps ST are connected to each other. The processor 120, the display 130, the memory 140, the user interface 150, and the controller 160 from among components of the mobile health care device 100 shown in FIG. 1 may be arranged in the main body MB. The main body MB may further include a watch module so that the mobile healthcare device 100 may also be used as a watch.

Some of the components of the sensor 110 may be arranged in the straps ST. For example, when the sensor 110 is used to detect the body impedance of a user wearing the device 100, the sensor 110 may include one or more input electrodes which apply a current to the user and one or more output electrodes which detect a voltage from the user. In this example, one or more input electrodes and output electrodes may be exposed to the outside and may contact the user.

As shown in FIGS. 2A and 2B, a first electrode module 210, which includes a first input electrode 211 and a first output electrode 212, is arranged on an inner surface STb which may be included in any one of the straps ST of the mobile health care device 100, and a second electrode module 220, which includes a second input electrode 221 and a second output electrode 222, may be arranged on an outer surface STa which may be included in any one of the straps ST.

In this example, the first electrode module 210 is exposed through an inner surface of the device and it is configured to contact an outer surface of the user. Also, the second electrode module 220 is exposed through an outer surface of the device, and is configured to be touched by a user.

As shown in FIGS. 2A and 2B, directions in which the first input electrode 211 and the first output electrode 212 are arranged on the inner surface of the STb and in which the second input electrode 221 and the second output electrode 222 are arranged on the outer surface of the STa may be perpendicular to a lengthwise direction of the straps ST, however, the exemplary embodiments are not limited thereto.

The first input electrode 211, the first output electrode 212, the second input electrode 221, and the second output electrode 222 are arranged on one of the straps ST. According to an exemplary embodiment, because both of the second input electrode 221 and the second output electrode 222, which are used to contact a body part of the user while the body impedance is measured, are arranged on one of the straps ST, user convenience may be improved.

Also, in some examples the first input electrode 211 and the first output electrode 212 respectively face the second input electrode 221 and the second output electrode 222. However, this example is merely one example and it is unnecessary for the first input electrode 211, the first output electrode 212, the second input electrode 221, and the second output electrode 222 to exactly face each other, respectively. Although it is described that the first electrode module 210 and the second electrode module 220 are arranged on one of the straps ST, the exemplary embodiments are not limited thereto. As another example, the first electrode module 210 may be arranged on one of the straps ST and the second electrode module 220 may be arranged on the other of the straps ST. As another example, at least one of the first electrode module 210 and the second electrode module 220 may be arranged on the main body MB. Also, the mobile healthcare device 100 may include one main body MB and one strap ST.

When a target user whose body impedance is to be measured wears the mobile healthcare device 100, the first electrode module 210 may contact the wrist of the user. Also, the second electrode module 220 may contact other body parts of the user on which the mobile healthcare device 100 is not disposed. For example, the second electrode module 220 may contact fingers, side surfaces of hands, palms, the other wrist, and the like. The second input electrode 221 and the second output electrode 222 may contact different fingers or may simultaneously contact a single finger to measure the body impedance. In the example shown in FIG. 3, the user wears the mobile healthcare device 100 on a left wrist and touches the second electrode module 220 with the right index finger f1.

When the size of the electrodes which detect the bio information is reduced, a contact resistance may occur when a body part of the user touches the electrodes. The contact resistance may change into noise while the body impedance is being measured. Accordingly, the mobile healthcare device 100 may obtain the state information using the body impedance after the contact resistance is removed.

The noise generated by the contact resistance is usually an exponential function. Accordingly, it may take a time varying with the resistance components of a contact interface to be multiplied by the capacitance components of the contact interface until the detection values are stabilized. When the size of the electrodes is decreased, a contact area is also decreased, and the resistance components are greatly increased. As a result, it may take a long time until the detection values are stabilized. Also, due to movements which occur while the small electrodes are in contact with a body part, a noise other than the contact resistance may be added to data during the first few seconds.

Figure 4:
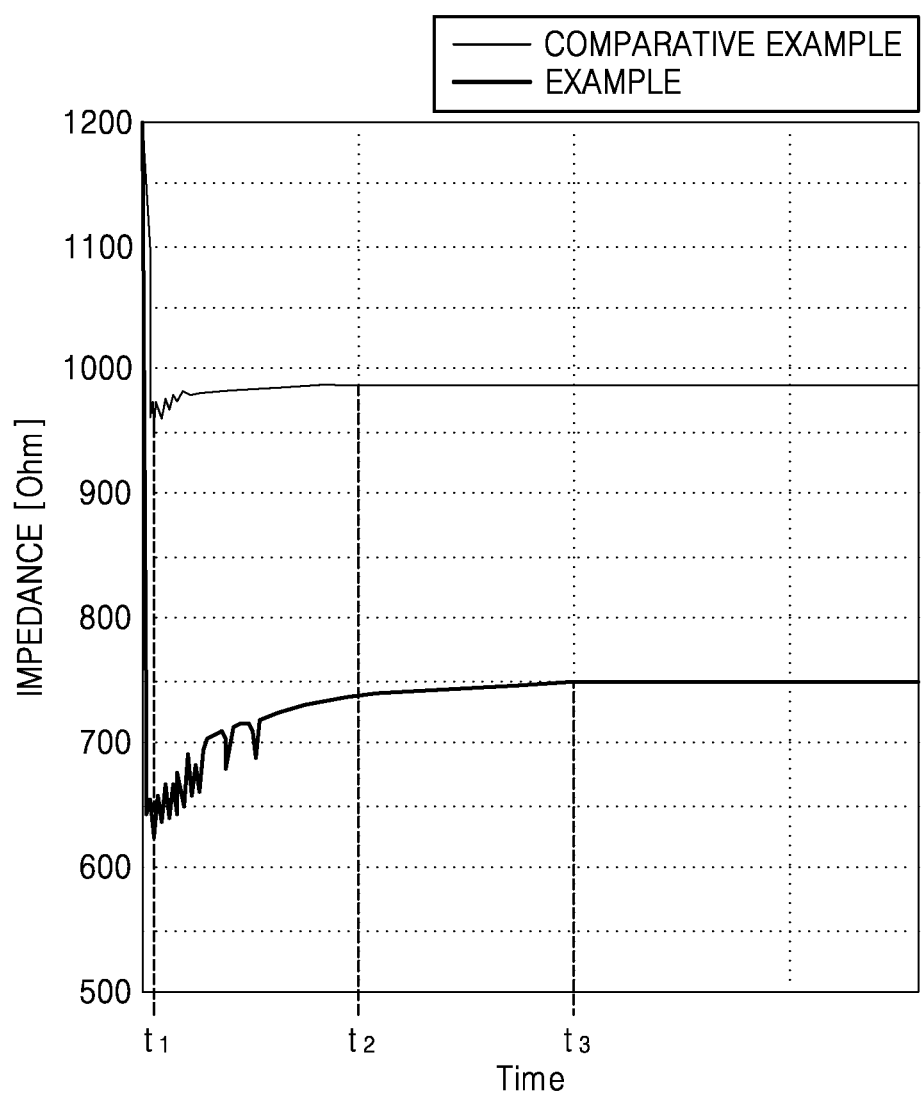
FIG. 4 is a graph showing an impedance change caused by a user contact, according to an exemplary embodiment.

FIG. 4 is a graph showing an impedance change caused by a user contact. Here, an area of an electrode in a comparative example is $1 \times 1$ cm$^2$, and an area of an electrode in the example is $0.5 \times 0.4$ cm$^2$. When the user wears the mobile healthcare device 100, the first electrode module 210 contacts the skin of the user. The second electrode module 220 may be contacted by another body part of the user at a point t1. As shown in FIG. 4, an impedance according to the comparative example and example greatly changes at the point t1 when the second electrode module 220 is contacted by the body part of the user.

In the comparative example, the impedance is stabilized at a point t2. However, because the sizes of electrodes according to the example are small, a contact resistance is generated at a time when the electrodes contact a body part of the user, and an impedance phase lag occurs due to the generated contact resistance. Therefore, in the example, the impedance is stabilized at a point t3 after more time has passed. The impedance phase lag may differ according to sizes of the electrodes, a contact area with the user, and the like, and may range from about 2 to about 10 seconds. The impedance phase lag may increase in proportion to a decrease of the area of the electrodes.

In an example in which an electrode module comes in contact with the user and the contact with the electrodes is terminated at a time that is within the impedance phase lag, the mobile healthcare device 100 may not detect the body impedance of the user. Accordingly, the mobile healthcare device 100 may provide a dynamic screen to guide the user to maintain a contact state.

Figure 5:
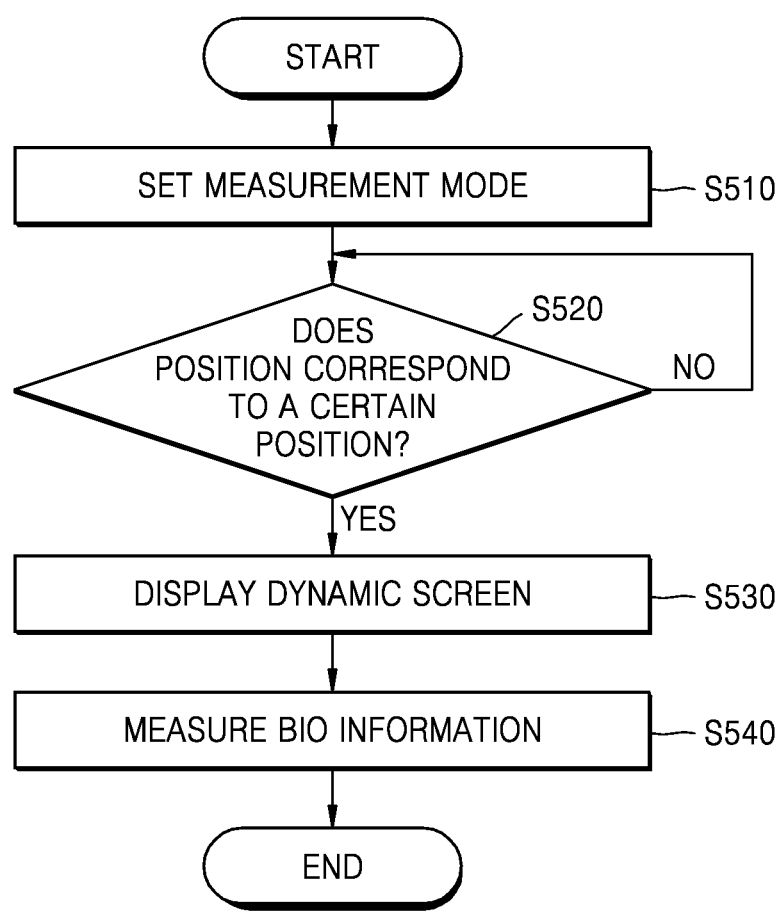
FIG. 5 is a flowchart of a method of operating the mobile healthcare device that is configured to display a dynamic screen, according to an exemplary embodiment.
Figure 6:
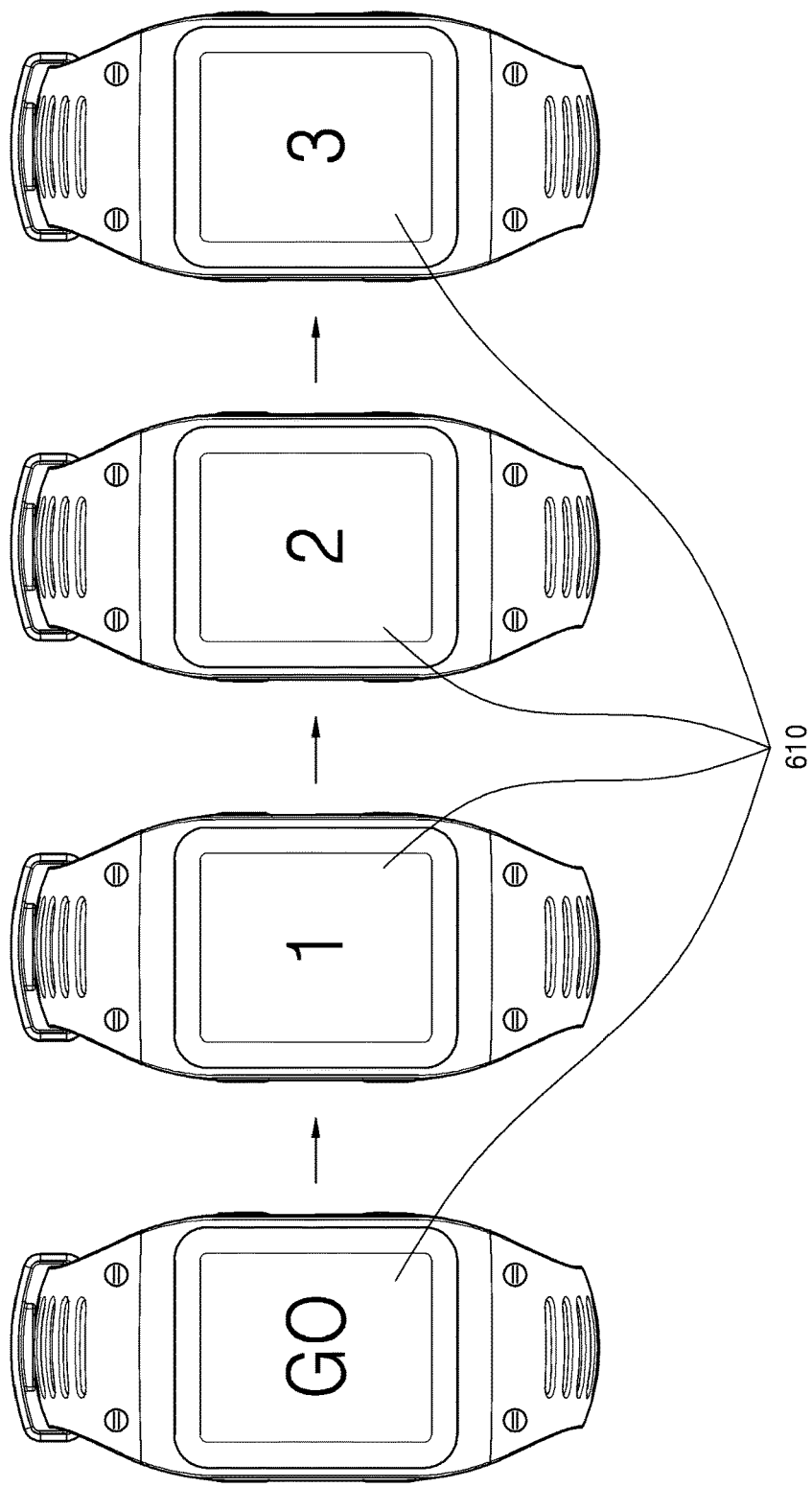
FIG. 6 is a reference view of a dynamic screen, according to an exemplary embodiment.

FIG. 5 is a flowchart of a method of operating the mobile healthcare device 100 when a dynamic screen is displayed, according to an exemplary embodiment, and FIG. 6 is a reference view of a dynamic screen, according to an exemplary embodiment. Referring to FIG. 5, the controller 160 may set a mode of the mobile healthcare device 100 to a measurement mode in operation S510. In some examples, the mobile healthcare device 100 may be set to a plurality of modes. For example, the mobile healthcare device 100 may include a clock mode in which time information is provided, a communication mode in which communication with an external device is available, a measurement mode in which the state information is obtained by detecting the bio information, and the like. When the user inputs a command for selecting the measurement mode among the plurality of modes, the controller 160 may set the mode to the measurement mode. If the mobile health care device 100 can operate in one mode only, the measurement mode may be set by a command for turning on the mobile healthcare device 100.

The controller 160 may determine whether a position of the user corresponds to a certain or predetermined position in operation S520. For example, the controller 160 may detect a position of the user based on a result received from the sensor 110 which detects the bio information. When the sensor 110 measures an impedance, the impedance output by the sensor 110 may differ according to whether the first electrode module 210 and the second electrode module 220 are in contact with the user.

When both of the first electrode module 210 and the second electrode module 220 are in contact with the user, the impedance output by the sensor 110 may dramatically change because noise may be generated due to a size of an area in which the sensor 110 contacts the user. For example, the controller 160 receives the impedance from the sensor 110, and if a value of the impedance with respect to a variation ratio of the impedance is greater than a reference value, the controller 160 may determine that the first electrode module 210 and the second electrode module 220 are in contact with the user. That is, the controller 160 may determine that the user is in a certain position or a body part is in a certain position.

If it is determined that the user is in a certain position (operation S520-YES), the controller 160 may display the dynamic screen on the display 130, in operation S530. In this example, the dynamic screen may be a screen for guiding the user to maintain the certain position. The dynamic screen may display an image that is changed entirely according to time, but may display an image including objects in which some of the objects are changed according to time.

For example, the dynamic screen may be a screen on which numbers change according to time. The numbers may change in an ascending order or a descending order according to time. FIG. 6 shows a dynamic screen 610 on which numbers change in the ascending order according to time. As another example, the dynamic screen may include an advertisement image. As another example, the dynamic screen may be a combination of an advertisement image and numbers which change according to time. Accordingly, a sense of dullness which may be caused when the user is in a certain position may be decreased by providing the dynamic screen.

The mobile healthcare device 100 may measure the bio information in operation S540. For example, the processor 120 may obtain the state information using the bio information received from the sensor 110. Although the sensor 110 may continue to detect the bio information in the measurement mode, the processor 120 may obtain the state information using the bio information which is detected after a certain or predetermined amount of time passes from a point in time at which the dynamic screen begins to be displayed. Also, the processor 120 may use the bio information which is detected after a display of the dynamic screen is stopped. As a non-limiting example, when the dynamic screen is displayed for ten seconds, the processor 120 may use the bio information which is detected after ten seconds from a time at which the dynamic screen is stopped being displayed. As another example, the processor 120 may use the bio information which is detected while the dynamic screen is being displayed. For example, the processor 120 may use the bio information which is detected after five seconds from the time when the dynamic screen begins to be displayed even though the dynamic screen continues to be displayed.

Because the state information is obtained using the bio information which is detected after a certain amount of time passes from the point at which the dynamic screen is stopped being displayed, the number of signal processing operations performed to remove noise may be reduced.

The sensor which detects the bio information has been described as an example of a sensor which detects a position of the user. However, the exemplary embodiments are not limited thereto, and other sensors for detecting a position of a user may be used.

If however, the user position is not in a certain position (operation S520-NO), then operation S520 repeats. For example, the repeating may be performed a threshold number of times, until the mobile healthcare device 100 is turned off, and the like.

Figure 7:
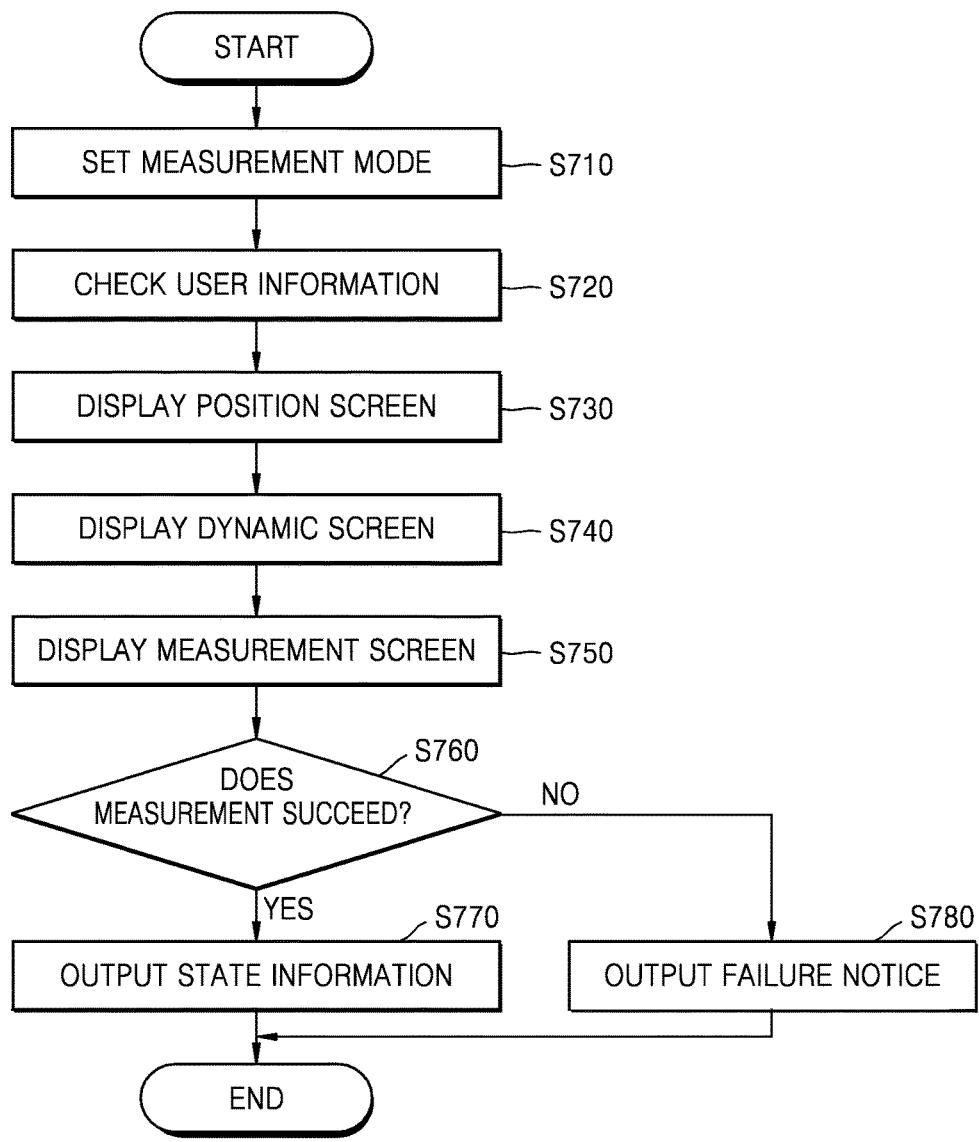
FIG. 7 is a flowchart of a method of operating the mobile health-care device that is configured to display a dynamic screen, according to another exemplary embodiment.
Figure 8A:
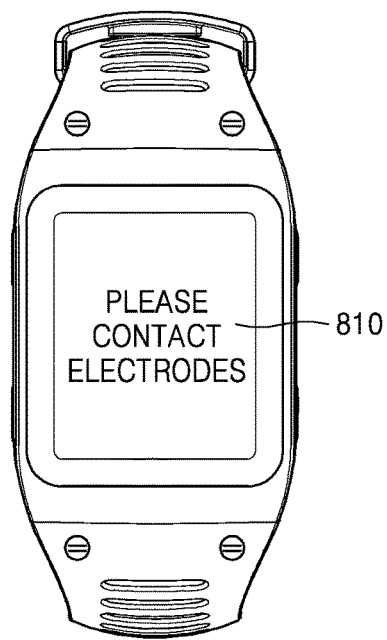
FIGS. 8A and 8B are reference views of guidance screens according to exemplary embodiments.
Figure 8B:
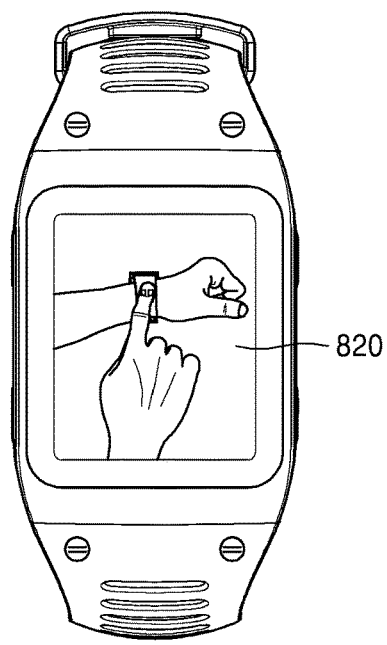
Figure 9:
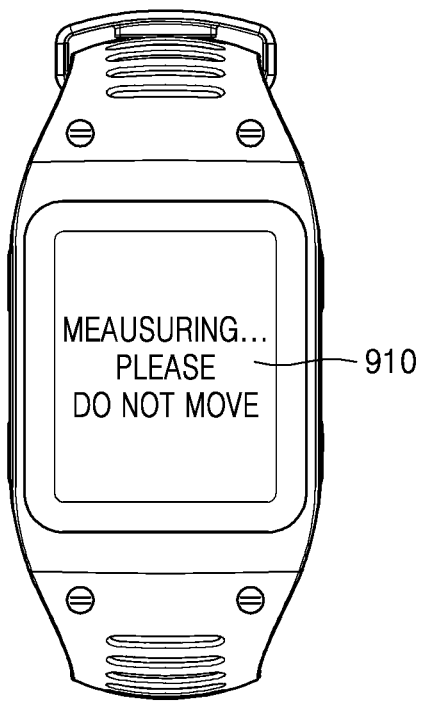
FIG. 9 is a reference view of a measurement screen according to an exemplary embodiment.

The mobile healthcare device 100 may measure the bio information by referring to the user information. FIG. 7 is a flowchart of a method of operating the mobile healthcare device 100 when a dynamic screen is displayed, according to another exemplary embodiment, FIGS. 8A and 8B are reference views of guidance screens according to exemplary embodiments, and FIG. 9 is a reference view of a measurement screen according to an exemplary embodiment. Referring to FIG. 7, the controller 160 may set the measurement mode according to a user command in operation S710.

The controller 160 may check the user information in operation S720. For example, the user information may be registered in the memory 140, may be input according to a user command, and the like. As another example, the user information may be uploaded after the mobile healthcare device 100 is synchronized with an external device (for example, a mobile terminal).

The controller 160 may display a position screen 810 on the display 130 in operation S730. The position screen 810 is a guidance screen for guiding the user to take a certain position. As shown in FIG. 8A, the controller 160 may display the position screen 810 as a text, or as shown in FIG. 8B, the controller 160 may display a position screen 820 as an image of a posture to be performed.

The controller 160 may display a dynamic screen in operation S740. For example, the controller 160 may display the dynamic screen after a certain amount of time passes from a point in time at which the position screen is displayed. For example, the dynamic screen may be displayed after 10 seconds from the time when the position screen is displayed. The controller 160 may also display the dynamic screen for a certain time. For example, the controller 160 may display the dynamic screen for 10 seconds, but the exemplary embodiments are not limited thereto. As described with reference to FIG. 5, the controller 160 may display the dynamic screen while the user is in a certain position and while the position screen is being displayed.

Also, the controller 160 may finish displaying the dynamic screen after a certain amount of time passes and may display a measurement screen in operation S750. For example, the processor 120 may display a measurement screen 910 as shown in FIG. 9. When the processor 120 obtains the state information using the bio information, the controller 160 may provide the user with an operation state of the mobile healthcare device 100 by displaying the measurement screen on the display 130 with the measurement screen indicating that the bio information is being measured. The processor 120 may measure the bio information while the dynamic screen is being displayed. In this example, the measurement screen may not be displayed.

If the measurement succeeds (operation S760-YES), the controller 160 may output the state information in operation S770. The controller 160 may determine that the measurement succeeds when the processor 120 obtains the state information. Then, the controller 160 may control the processor 120 to display the obtained state information on the display 130. For example, the state information may be displayed as a graph according to time when the state information is being output. Also, the controller 160 may determine whether the state information is normal or abnormal by referring to the user information and may output a determination result.

If the measurement fails (operation S760-NO), the controller 160 may output a failure notice which indicates that the measurement has failed in operation S780. If the processor 120 does not obtain the state information, the controller 160 may determine that the measurement has failed. For example, the controller 160 may terminate the measurement mode after the failure notice is output or may display a screen for starting the measurement again. For example, the controller 160 may display the position screen, the dynamic screen, or the like, and the mobile healthcare device 100 may perform an operation for measuring the bio information again.

A plurality of users may use the mobile healthcare device 100. Alternatively, a guest may temporarily use the mobile healthcare device 100. A method of managing the obtained state information may vary according to types of the user information. For example, the measurement mode of the mobile healthcare device 100 may include a user mode in which the user information matches the state information and the user information and the state information are automatically stored, and a guest mode in which the user information and the state information are automatically discarded if there is no command for storing the user information and the state information.

Figure 10:
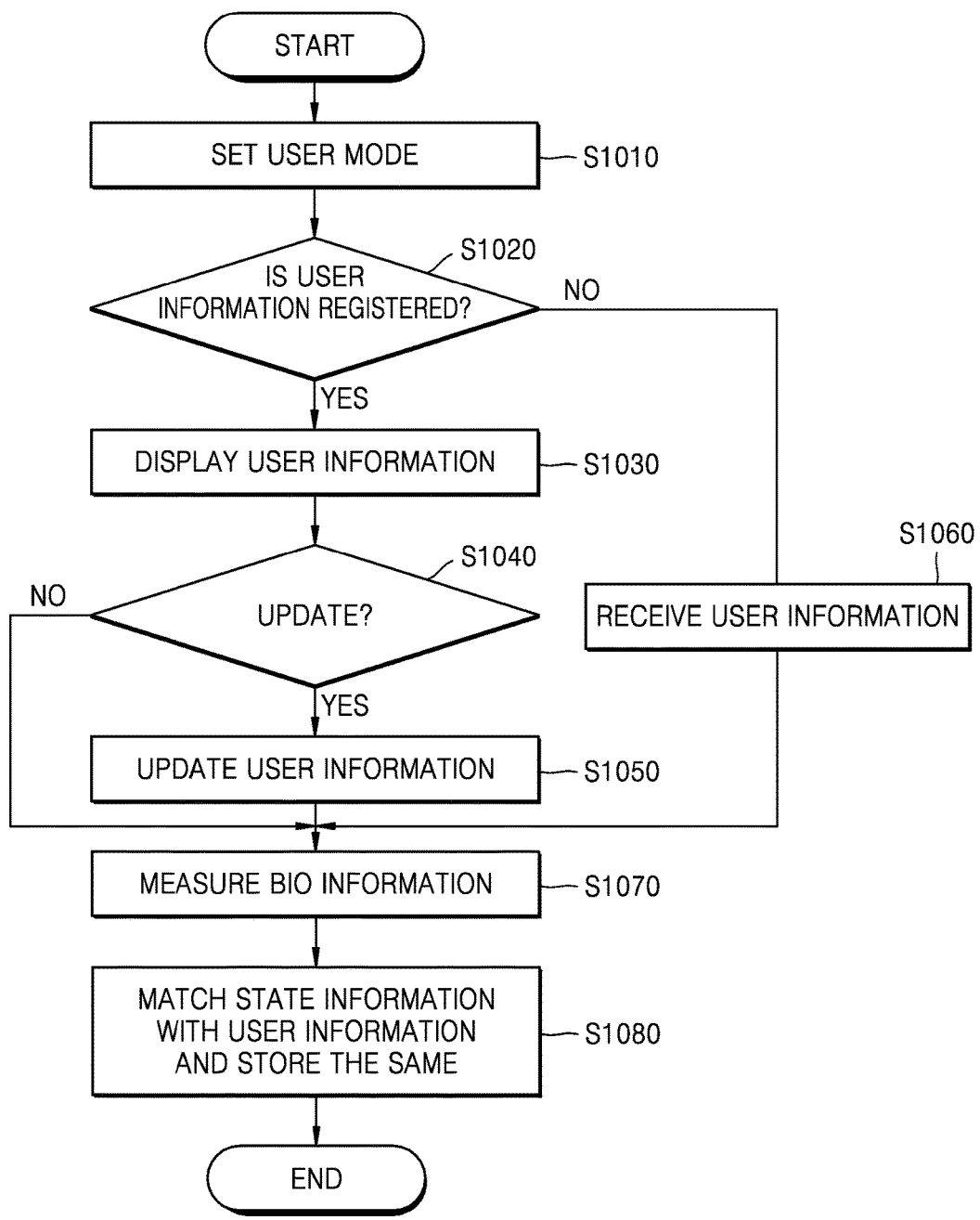
FIG. 10 is a flowchart of a method of managing user information and state information in a user mode, according to an exemplary embodiment.

FIG. 10 is a flowchart of a method of managing the user information and the state information in the user mode, according to an exemplary embodiment.

Referring to FIG. 10, based on a user command, the controller 160 may set the measurement mode of the mobile healthcare device 100 to the user mode in operation S1010. In the measurement mode, for example, the controller 160 may display a list including a user mode and a guest mode. The user may input a command for selecting the user mode, and then the controller 160 may set the measurement mode to the user mode.

In operation S1020, the controller 160 may determine whether the user information is registered in the memory.

If it is determined that the user information is registered (operation S1020-YES), the controller 160 may display the registered user information in operation S1030. If there are a plurality of users, the controller 160 may display a user list (for example, a user 1, a user 2, etc.). If a user command for selecting any one of the users is received, user information with regard to the selected user may be displayed. However, if there is only one user, the controller 160 may display user information with regard to the single user without displaying a user list. For example, the user information may include a height, a weight, an age, a gender, a name, contact information, and the like, of the user. If the user information includes multiple pieces of information, the multiple pieces of information may be displayed on a single screen, each piece may be sequentially displayed on a single screen, and the like.

If a user command for updating one of the displayed pieces of information is received (operation S1040-YES), the controller 160 may update the user information in operation S1050. If a user command for updating a piece of information is not received (operation S1040-NO), operation S1050 is skipped.

Returning again to S1020, if it is determined that no user information is registered (operation S1020-NO), the controller 160 may receive the user information in operation S1060. For this purpose, the controller 160 may display a list of items for user information on the display 130 in order to guide the user to record the user information in each of the items. Accordingly, the user may input the user information as guided by the controller 160, and the controller 160 may receive the user information. The user information may be checked through the above operations.

The mobile healthcare device 100 may determine the bio information in operation S1070. An example of an operation of measuring the bio information has been described with reference to FIGS. 5 and 7. That is, after the dynamic screen for guiding the user to maintain a certain position is displayed, the state information may be obtained using the bio information received from the sensor 110. Then, the obtained state information may be output.

The controller 160 matches the state information with the user information and may store the state information and the user information in operation S1080. In some examples, a history of the state information of the user may be obtained by matching and storing the state information and the user information.

Figure 11:
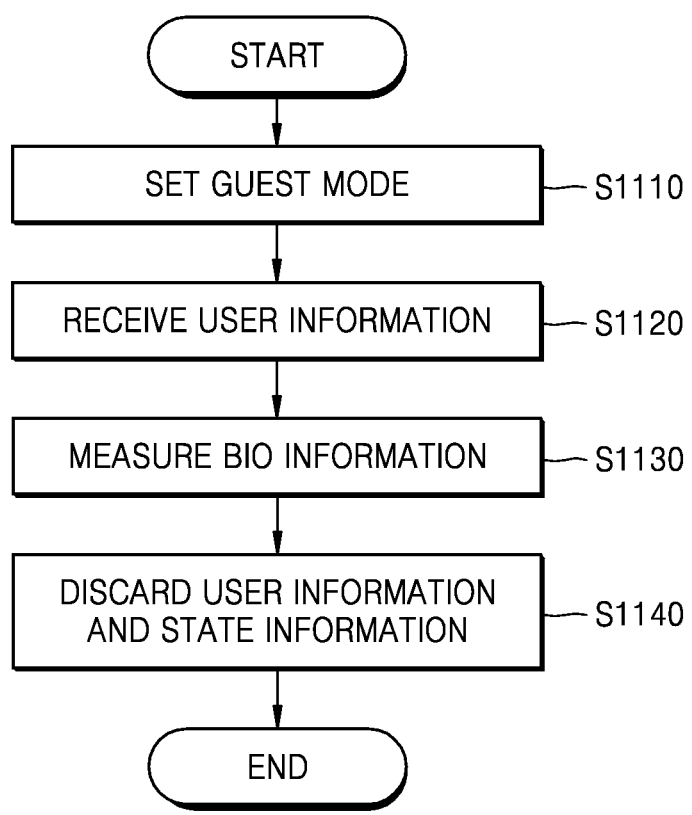
FIG. 11 is a flowchart of a method of managing user information and state information in a guest mode, according to an exemplary embodiment.

FIG. 11 is a flowchart of a method of managing the user information and the state information in a guest mode, according to an exemplary embodiment.

Referring to FIG. 11, in operation S1110, the controller 160 may set the measurement mode to the guest mode according to a user command. For example, the controller 160 may display a measurement mode list in the measurement mode. For example, the measurement mode list may include a user mode and a guest mode. The user may input a command for selecting the guest mode, and the controller 160 may set the measurement mode to the guest mode.

The controller 160 may receive the user information in operation S1120. For example, the controller 160 may display items of the user information on the display 130 and may guide the user to record the user information in each item of the user information. The user inputs the user information as guided by the controller 160, and the controller 160 may receive the user information.

The mobile healthcare device 100 may measure the bio information in operation S1130. An example of a method of measuring the bio information has been described above.

The controller 160 may discard the state information and the user information in operation S1140. The controller 160 may discard the state information and the user information instead of storing the same if the mode of the mobile healthcare device 100 is changed. For example, when the measurement mode is terminated, the controller 160 may discard the state information and the user information. As another example, when a user command for changing the measurement mode to the user mode or for measuring state information for a new guest is input, the state information and the user information may be discarded. Personal information of the user may be protected by discarding the state information and the user information which are measured in the guest mode.

Although the body impedance, which corresponds to the bio information and requests the user to maintain a certain position, has been described, the exemplary embodiments are not limited thereto. When a PPG is read, the PPG may differ according to a difference between a height of the heart and that of the sensor 110. The mobile healthcare device 100 may provide a dynamic screen so that the sensor 110 may be placed at the same height with the heart. As another example, the dynamic screen may be provided to prevent a generation of motion artifacts. The dynamic screen for preventing the generation of motion artifacts may be displayed for a threshold amount of time such as 2 seconds to 5 seconds.

With the developments in medical science and the extension of life expectancy, interest in healthcare and medical devices has increased. Accordingly, various medical devices for use in hospitals and inspection agencies, and medium-sized medical devices installed in governmental agencies have been proposed.

In some examples, noise may be easily added to initial data acquired from a body because of a small contact area of a watch-type body fat analyzer. According to one or more exemplary embodiments, a page count operation is performed before a body fat measurement such that enough time for stabilizing a position of a user can be secured.

It should be understood that the exemplary embodiments described herein should be considered in a descriptive sense only and not for purposes of limitation. Descriptions of features or aspects within each exemplary embodiment should also typically be considered as available for other similar features or aspects in other exemplary embodiments.

While one or more exemplary embodiments have been described with reference to the figures, it should be understood by those of ordinary skill in the art that various changes in form and details may be made therein without departing from the spirit and scope as defined by the following claims.

What is claimed is:

1. A method of operating a mobile healthcare device, the method comprising:
   setting, by a processor, a current mode of the mobile healthcare device to a measurement mode;
   displaying, by a display, a position screen for guiding a user to take a predetermined position indicating that the user simultaneously contacts first electrodes and second electrodes of the mobile healthcare device;
   measuring, by the first electrodes and the second electrodes, an impedance of the user;
   determining, by the processor, whether a user position of the user corresponds to the predetermined position, by comparing the impedance that is measured, with a predetermined value;

replacing, by the display, the position screen that is displayed by displaying a dynamic screen for guiding the user to maintain the predetermined position during the measurement mode, in response to the user position being determined to correspond to the predetermined position, the dynamic screen being at least partially different from the position screen;

determining, by the processor, whether a predetermined amount of time passes from a point in time at which the dynamic screen begins to be displayed;

obtaining, by the processor, state information of the user, based on an impedance that is measured while the dynamic screen is displayed, in response to the predetermined amount of time being determined to pass from the point in time at which the dynamic screen begins to be displayed; and displaying, by the display, the state information that is obtained.

2. The method of claim 1, wherein the predetermined amount of time ranges from about two seconds to about ten seconds.

3. The method of claim 1, further comprising stopping the displaying of the dynamic screen, in response to the predetermined amount of time being determined to pass from the point in time at which the dynamic screen begins to be displayed, wherein the obtaining of the state information of the user is performed after the displaying of the dynamic screen is stopped.

4. The method of claim 1, wherein the obtaining of the state information of the user is performed during the displaying of the dynamic screen.

5. The method of claim 1, wherein the dynamic screen displays numbers that change according to time.

6. The method of claim 5, wherein the numbers sequentially and continuously change in an ascending order or descending order.

7. The method of claim 1, further comprising storing user information comprising any one or any combination of a height, a gender, and a weight of the user.

8. The method of claim 7, further comprising:
matching the state information that is obtained, with the user information; and
storing the state information and the user information that are matched, in response to the measurement mode being a user mode.

9. The method of claim 7, further comprising discarding the state information that is obtained and the user information, in response to the measurement mode being a guest mode.

10. The method of claim 7, further comprising discarding the state information that is obtained and the user information, in response to the measurement mode being terminated.

11. The method of claim 1, wherein the state information of the user comprises a bio composition of the user.

12. The method of claim 11, wherein the bio composition of the user comprises any one or any combination of body fat, a skeletal muscle mass, a muscle mass, a degree of obesity, a muscle strength, an edema value, a body composition ratio, and an amount of intra-abdominal fat.

13. A mobile healthcare device comprising:
first electrodes and second electrodes configured to measure an impedance of a user;
a display;
a processor configured to:
control the display to display a position screen for guiding the user to take a predetermined position indicating that the user simultaneously contacts the first electrodes and the second electrodes;
determine whether a user position of the user corresponds to the predetermined position, by comparing the impedance that is measured, with a predetermined value;
control the display to replace the position screen that is displayed by displaying a dynamic screen for guiding the user to maintain the predetermined position, in response to the user position being determined to correspond to the predetermined position, the dynamic screen being at least partially different from the position screen;
determine whether a predetermined amount of time passes from a point in time at which the dynamic screen begins to be displayed;
obtain state information of the user, based on an impedance that is measured while the dynamic screen is displayed, in response to the predetermined amount of time being determined to pass from the point in time at which the dynamic screen begins to be displayed; and
control the display to display the state information that is obtained.

14. The mobile healthcare device of claim 13, wherein the dynamic screen displays numbers that change according to time.

15. The mobile healthcare device of claim 13, wherein the processor is further configured to, in response to the predetermined amount of time being determined to pass from the point in time at which the dynamic screen begins to be displayed, control the display to replace the dynamic screen that is displayed by displaying a measurement screen indicating that the impedance of the user is being measured, while the state information of the user is being obtained.

16. The mobile healthcare device of claim 13, wherein the processor is further configured to:
determine whether the state information of the user is successfully obtained;
control the display to display the state information that is obtained, in response to the state information being determined to be successfully obtained; and
control the display to display a failure notice indicating that the impedance of the user is failing to be measured, in response to the state information being determined to be unsuccessfully obtained.

* * * * *